United States Patent [19]
Hacker et al.

[11] Patent Number: 5,599,769
[45] Date of Patent: Feb. 4, 1997

[54] SYNERGISTIC HERBICIDAL COMPOSITIONS COMPRISING GLYPHOSATE OR GLUFOSINATE IN COMBINATION WITH A SULFONYLUREA HERBICIDE

[75] Inventors: Erwin Hacker, Hochheim am Main; Manfred Röttele; Walter Dannigkeit, both of Kelkheim; Martin Hess, Mainz; Hans Schumacher, Flörsheim am Main, all of Germany

[73] Assignee: Hoechst Aktiengesellschaft, Frankfurt, Germany

[21] Appl. No.: 462,119

[22] Filed: Jun. 5, 1995

Related U.S. Application Data

[63] Continuation of Ser. No. 231,999, Apr. 21, 1994, abandoned, which is a continuation of Ser. No. 50,291, May 11, 1993, abandoned.

[30] Foreign Application Priority Data

Nov. 13, 1990 [DE] Germany .......................... 40 36 069.5

[51] Int. Cl.$^6$ .......................... A01N 43/54; A01N 43/66; A01N 57/04
[52] U.S. Cl. .......................... 504/128
[58] Field of Search .......................... 504/128

[56] References Cited

U.S. PATENT DOCUMENTS

| | | | |
|---|---|---|---|
| 4,168,963 | 9/1979 | Rupp et al. | 504/206 |
| 4,830,658 | 5/1989 | Bieringer et al. | 504/128 |
| 5,104,443 | 4/1992 | Kehne et al. | 71/92 |

FOREIGN PATENT DOCUMENTS

| | | |
|---|---|---|
| 0192583 | 8/1986 | European Pat. Off. . |
| 0318276 | 5/1989 | European Pat. Off. . |
| 0387165 | 9/1990 | European Pat. Off. . |
| 0431545 | 6/1991 | European Pat. Off. . |
| 0252237 | 1/1988 | Germany . |
| WO89/04606 | 6/1989 | WIPO . |
| WO90/02486 | 3/1990 | WIPO . |
| WO90/07275 | 7/1990 | WIPO . |

OTHER PUBLICATIONS

Patent Abstracts of Japan, vol. 11, No. 60, C405 abstract from JP 61–218503, published 1986–09–29 Nissan Chem Ind Ltd et al.

Northeastern Weed Science Society, vol. 42, 1988, Proceedings, S. B. Horsley: "Tank mixing glyphosate with adjuvants and other herbicides for striped maple control", p. 84.

*Primary Examiner*—S. Mark Clardy
*Attorney, Agent, or Firm*—Curtis, Morris & Safford, P.C.

[57] ABSTRACT

Synergistically increased effects against undesirable plant growth are achieved by a combined application of an active substance of the type A with an active substance of the type B, where type A represents the herbicides glufosinate (A1), glyphosate (A2), or salts thereof, and type B represents sulfonyl ureas of the formula (B)

$$R^1-SO_2-NH-\overset{O}{\underset{\|}{C}}-N\underset{R^2}{\overset{R^3}{\diagup}}\diagdown\hspace{-4pt}\bigcirc\hspace{-4pt}\diagup\hspace{-4pt}\diagdown\hspace{-4pt}X \quad (B)$$

where
$R^1$ is a radical from the group comprising 2-ethoxyphenoxy, 2-propoxyphenoxy, 2-isopropoxyphenoxy, 2-methoxycarbonylphenyl, 3-(dimethylaminocarbonyl)-pyrid-2-yl, 3-ethylsulfonylpyrid-2-yl, 3-[N-($C_1$–$C_4$-alkyl)-N-($C_1$–$C_4$-alkylsulfonyl)amino]pyrid-2-yl, (N-methyl-N-methylsulfonyl)aminosulfonyl, 2-(2-chloroethoxy)phenyl, 2-(methoxycarbonyl)phenyl, 2-(meth-oxycarbonyl)thien-3-yl,
with the remaining substituents as defined herein.

14 Claims, No Drawings

SYNERGISTIC HERBICIDAL COMPOSITIONS COMPRISING GLYPHOSATE OR GLUFOSINATE IN COMBINATION WITH A SULFONYLUREA HERBICIDE

This application is a continuation of application Ser. No. 08/231,999, abandoned, filed Apr. 21, 1994, which in turn is a continuation of application Ser. No. 08/050,291, filed May 11, 1993, now abandoned, filed under 35 USC 371 from PCT application PCT/EP91/02068, filed Nov. 2, 1991.

The invention is in the field of the crop protection agents which can be used against monocotyledon and dicotyledon weeds.

Glufosinate-ammonium (phosphinothricin-ammonium) is a known herbicide which is taken up via the green parts of the plant (foliar-acting herbicide); see "The Pesticide Manual" 8th Edition, British crop Protection Council 1987, p. 448. Glufosinate-ammonium is mainly used post-emergence for controlling weeds and grass weeds in plantation crops and on areas which are not under cultivation and also, by means of specific application techniques, for treatment between rows in agricultural field crops such as corn, cotton etc.

Glyphosate is also a known herbicide for controlling annual and perennial weeds and grass weeds. It also acts via post-emergence application and foliar uptake; cf. the above-mentioned "The Pesticide Manual", p. 449.

Application is mainly carried out in plantation crops and on areas which are not under cultivation. In the case of commercially available products, the monoisopropyl ammonium salt of glyphosate is used.

Surprisingly, some herbicidal active substances have now been found in biological tests which, when applied together with glufosinate-ammonium or glyphosate, result in pronounced synergistically increased effects.

The present invention relates to herbicidal compositions with a herbicidally effective content of a combination of A) one or more compounds of the formulae (A1) and (A2)

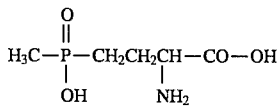   (A1)

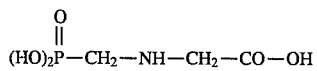   (A2)

or salts thereof and

B) one or more compounds of the formula (B)

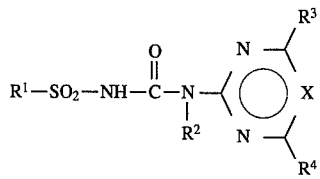   (B)

where $R^1$ is a radical from the group comprising 2-ethoxyphenoxy, 2-propoxyphenoxy, 2-isopropoxyphenoxy, 2-methoxycarbonylphenyl, 3-(dimethylaminocarbonyl)-pyrid-2-yl, 3-ethylsulfonylpyrid-2-yl, 3-[N-($C_1$–$C_4$-alkyl)-N-($C_1$–$C_4$-alkylsulfonyl)amino]pyrid-2-yl, (N-methyl-N-methylsulfonyl)aminosulfonyl, 2-(2-chloroethoxy)phenyl, 2-(methoxycarbonyl)phenyl, 2-(methoxycarbonyl)thien-3-yl, $R^2$ is H or methyl, $R^3$ and $R^4$ independently of one another are $C_1$–$C_2$-alkyl, $C_1$–$C_2$-alkoxy or $C_1$–$C_2$-haloalkoxy and X is CH or N, or salts thereof, with the exception of the combinations of a compound of the formula (A2) with one or more compounds of the formula (B) in which a) $R^1$ is 2-methoxycarbonylphenyl, $R^2$ is H or methyl and $R^3$ is methyl, $R^4$ is methoxy and X is N, and b) $R^1$ is 2-(methoxycarbonyl)thien-3-yl, $R^2$ is H, $R^3$ is methyl, $R^4$ is methoxy and X is N.

Preferred salts of the compounds of the formula A1 and A2 are ammonium salts, mono-, di- and trialkylammonium salts, alkali metal salts and alkaline earth metal salts. The monoammonium salt of glufosinate (A1-1) and the monoisopropylammonium salt of glyphosate (A2-1) are particularly preferred. Glufosinate exists in the D- and L-form and mixtures of these, for example in the form of a racemate. Formula A1 embraces all abovementioned spatial configurations and their mixtures, preference being given to the racemate and to the L-form and their mixtures.

Compounds of the formula (B) can form salts with bases in which the hydrogen of the $SO_2NH$ group is replaced by a cation which is suitable for agriculture, for example metal salts such as alkali metal salts or alkaline earth metal salts, or ammonium salts or salts with organic amines. Acid addition salts with, for example, HCl, HBr, $H_2SO_4$ and $HNO_3$ are also possible.

Examples of suitable compounds of the formula (B) are

1-[(2-ethoxyphenoxy)sulfonyl]-3-(4,6-dimethoxypyrimid-2-yl)urea (B1),

1-[(2-n-propoxyphenoxy)sulfonyl]-3-(4,6-dimethoxypyrimid-2-yl )urea (B2),

1-[(2-isopropoxyphenoxy)sulfonyl]-3-(4,6-dimethoxypyrimid-2-yl)urea (B3),

1-[(2-methoxycarbonylphenyl)sulfonyl]-3-[4,6-bis(difluoromethoxy)pyrimid-2-yl]urea (B4; primisulfuron-methyl, CGA 136872), 1-[(3-dimethylaminocarbonylpyridin-2-yl)sulfonyl]-3-(4,6-dimethoxypyrimidin-2-yl)urea (B5; nicosulfuron, SL-950), 1-[(3-ethylsulfonylpyridin-2-yl)sulfonyl]-3-(4,6-dimethoxypyrimid-2-yl)urea (B6; DPX-E 9636), 1-[3-(N-methyl-N-methylsulfonylamino)pyrid-2-ylsulfonyl]-3-(4,6-dimethoxypyrimid-2-yl)urea (B7), 1-[3-(N-ethyl-N-methylsulfonylamino)pyrid-2-ylsulfonyl]-3-(4,6-dimethoxypyrimid-2-yl)urea (B8), 1-[3-(N-methyl-N-ethylsulfonylamino)pyrid-2-ylsulfonyl]-3-(4,6-dimethoxypyrimid-2-yl)urea (B9), 1-[3-(N-methyl-N-methylsulfonylamino)pyrid-2-ylsulfonyl]-3-(4,6-dimethylpyrimid-2-yl)urea (B10), 1-[3-(N-methyl-N-methylsulfonylamino)pyrid-2-ylsulfonyl]-3-(4-methoxy-6-methylpyrimid-2-yl)urea (B11), 1-(N-methyl-N-methylsulfonylaminosulfonyl)-3-(4,6-dimethoxypyrimid-2-yl)urea (B12; amidosulfuron), 1-(2-methoxycarbonylthien-3-ylsulfonyl)-3-(4-methoxy-6-methyl-1,3,5-triazin-2-yl)urea (B13; thiameturonmethyl, BPX-M 6316), 1-[2-(2-chloroethoxy)phenylsulfonyl]-3-(4-methoxy-6-methyl-1,3,5-triazin-2-yl)urea (B14; triasulfuron)

1-[(2-methoxycarbonylphenyl)sulfonyl]-3-(4-methoxy-6-methyl-1,3,5-triazin-2-yl)urea (B15; metsulfuronmethyl, DPX 6376), and 1[(2-methoxycarbonylphenyl)sulfonyl]-3-methyl-3-(4-methoxy-6-methyl-1,3,5-triazin-2-yl)urea (B16; tribenuron-methyl, DPX-L 5300 ).

Preference is given to herbicidal compositions according to the invention with combinations of the compound (A1-1) with one or more compounds from the group (B1) to B16), in particular (B1), (B2), (B3), (B5), (B7), (B8), (B9), (B10), (B11), (B13) and (B16).

Preference is furthermore given to herbicidal compositions according to the invention with combinations of the compound (A2-1) with one or more compounds from the group (B1) to (B12), in particular (B1), (B2), (B3), (B5) and (B12).

The compounds of the formulae (B1) to (B3) are 1-[(2-alkoxyphenoxy)sulfonyl]-3-(4,6-dimethoxypyrimid2-yl)ureas and disclosed in EP-A-0,342,569. Applied pre- and post-emergence, they are tolerated by the annual crop plant species such as cereals, rice and corn. The effect covers a broad spectrum of annual and perennial weed species, grass weed species and Cyperaceae species.

The compound of the formula (B4) (pirimisulfuron) is known from Brighton Crop Protection Conference-Weeds1987, p. 41–48.

The compound of the formula (B5) is known under the name of nicosulfuron or SL-950 (see F. Kimura et al., Brighton Crop Protection Conference-Weeds-1989, pages 29–34). Nicosulfuron (SL-950), i.e. 3-(4,6-dimethoxypyrimidin-2-yl)-1-(3-dimethylaminocarbonylpyridin-2-ylsulfonyl)urea, is a sulfonylurea herbicide which has been employed to date mainly for controlling grasses and broadleaved weeds in corn. Applied post-emergence, a large number of annual and perennial weeds and grass weeds are controlled.

The compound of the formula (B6) (DPX-E 9636) is known from Brighton Crop Protection Conf.-Weeds-1989, p. 23 et seq.

The compounds of the formula (B7) to (B11) have been disclosed in German Patent Application P 4,000,503.8.

Amidosulfuron (B12) has been disclosed in EP-A-0,131, 258 and is known from Z. Pfl. Krankh. Pfl. Schutz, Supplement XII, p. 489–497 (1990).

Compounds (B13) to (B16) are described in Farm Chemicals Handbook '90, Meister Publishing Company, Willoughby, Ohio, USA (1990).

All the abovementioned herbicides have in common that they are taken up post-emergence via the leaves (partly or completely) and act in this manner.

Some combinations of compounds of the formula (A2) and sulfonylureas are already known; see S. B. Horsley, Proc. Northeast. Weed Sci. Soc. 42, 84 (1988); H. R. Mashadi and J. O. Evans, Res. Prog. Rep. West. Soc. Weed Sci. 1987 Meet., 348–50; K. E. Bowren, G. S. Noble, Res. Rep. Expert Comm. Weeds West. Can. (33 Meet.) Vol. 2, 240 (1986); D. G. Pchajek, J. D. Gingerich, Res. Rep. Expert Comm. Weeds West. Can. (34 Meet.) Vol. 2, 524–26 (1987).

The herbicidal compositions according to the invention have an excellent herbicidal activity against a broad spectrum of economically important monocotyledon and dicotyledon noxious plants.

If the active substance combinations are applied post-emergence to the green parts of the plant, growth stops dramatically very soon after the treatment, and the weed plants remain in the growth stage of the time of application, or die more or less rapidly after a certain period of time. The weeds are controlled very effectively in this manner. When used for controlling weeds in plantations, competition by the weeds, which is harmful to the crop plants, is eliminated in a sustained manner by using the novel compositions according to the invention.

For example, using the active substance combinations according to the invention, a herbicidal action is achieved which exceeds what would have been expected as an additive action of the individual components. Such increased effects permit the dosage rates of the individual active substances to be reduced substantially. While the dosage rates are comparable, the weed-grass weed spectrum controlled is much broader by virtue of the synergistic effects. At the same time, properties which are of the utmost importance in practical use are considerably improved in the case of most combinations. These include, for example, the speed of action, the long-term action, the flexibility upon use, etc. This permits comprehensive, rapid, sustained and economical control of weeds and grass weeds. Such properties are therefore economically progressive because they offer considerable advantages to the user in practical weed control by allowing him to control weeds more economically or more rapidly or in a more sustained manner, therefore obtaining higher yields in a stand of crop plants.

The selection of the ratios by weight and dosage rates depend, for example, on the components in the mixture, the development stage of the weeds or grass weeds, the weed spectrum, environmental factors and climatic conditions.

The ratios by weight A:B can therefore vary within wide limits and are generally at 1500:1 to 1:10, based on weight.

Ratios by weight of 200:1 to 1:2, in particular 50:1 to 5:1, are preferably used.

The dosage rates of the herbicides A in the active substance combinations are preferably between 10 and 2500 g/ha, based on active ingredient. Glufosinate is preferably applied in amounts of 10 to 1200 g/ha, and glyphosate is preferably applied in amounts of 500 to 2000 g/ha. The dosage rates of compounds of type B are generally from 2 to 200 g/ha, preferably from 2 to 120 g/ha, in particular from 2 to 100 g/ha, based on active ingredient.

The active substance combinations according to the invention can exist either as mixed formulations of the two components, which are then applied in the customary manner after dilution with water, or can be prepared in the form of so-called tank mixes by conjointly diluting the components, formulated separately, with water.

Compounds A and B or their combinations can be formulated in many ways, depending on the biological and/or chemico-physical parameters. The following possibilities are therefore suitable for formulation: wettable powders (WP), emulsifiable concentrates (EC), aqueous solutions (SL), emulsions (EW) such as oil-in-water or water-in-oil emulsions, sprayable solutions or emulsions, dispersions on an oil or water base, suspo-emulsions, dusting agents (DP), seed-dressing agents, granules for soil application or for broadcasting, water-dispersible granules (WG), ULV formulations, microcapsules or waxes.

These individual formulation types are known in principle and are described, for example, in: Winnacker-Küchler, "Chemische Technologie [Chemical Technology]", Volume 7, C. Hauser Verlag Munich, 4th Ed. 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives, are also known and are described, for example, in: Watkins, "Handbook of Insecticide Dust Diluents and Carriers", nd Ed., Darland Books, Caldwell N.J.; H.v.Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte [Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, such as other herbicides, fungicides or insecticides, and also safeners, fertilizers and/or growth regulators may also be prepared on the basis of these formulations, for example in the form of a readymix or as a tank mix.

Wettable powders are preparations which are uniformly dispersible in water and which, besides the active substance, also contain wetting agents, for example polyoxethylated alkylphenols, polyoxethylated fatty alcohols or fatty amines, fatty alcohol polyglycol ether sulfates,, alkanesulfonates or alkylbenzenesulfonates, and dispersing agents, for example sodium lignin-sulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active substance in an organic solvent, for example butanol, cyclohexanone, dimethylformamide, xylene or else higher-boiling aromatic compounds or hydrocarbons, with the addition of one or more emulsifiers. Examples of emulsifiers which can be used are: calcium salts of an alkylarylsulfonic acid, such as Ca dodecylbenzene-sulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents can be obtained by grinding the active substance with finely divided solid substances, for example talc or natural clays, such as kaolin, bentonite, pyrophyllite or diatomaceous earth.

Granules can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, the agrochemical preparations contain 0.1 to 99 percent by weight, in particular 2 to 95% by weight, of active substances A+B. In the formulations, the active substances A+B can exist in various concentrations.

The concentration of active substance in wettable powders is, for example, approx. 10 to 95% by weight, the remainder to 100% is composed of customary formulation auxiliaries. In the case of emulsifiable concentrates, the active substance concentration can be approx. 1 to 85% by weight, preferably 5 to 80% by weight.

Formulations in the form of dusts contain approx. 1 to 25% by weight, usually 5 to 20% by weight, of active substance, sprayable solutions approx. 0.2 to 25% by weight, preferably 2 to 20% by weight, of active substance. In the case of granules such as water-dispersible granules, the active substance content depends partly on whether the active compound is liquid or solid, and which granulation auxiliaries and fillers are used. As a rule, the water-dispersible granules have a content of between 10 and 90% by weight.

In addition, the active substance formulations mentioned contain, if appropriate, the adhesives, wetting agents, dispersing ,agents, emulsifiers, penetrants, solvents, fillers or carriers which are conventional in each case.

For use, the formulations, present in commercially available form, are diluted, if appropriate, in a customary manner, for example using water in the case of wettable powders, emulsifiable concentrates, dispersions and water-dispersible granules. Preparations in the form of dusts, soil granules or granules for broadcasting, and also sprayable solutions are usually not further diluted with other inert substances before use.

The joint application of the active substances in the form of tank mixes is preferred, in which case the concentrated formulations of the individual active substances which are formulated optimally are conjointly mixed with water in the tank, and the resulting slurry is applied.

The examples which follow are intended to illustrate the invention:

A. Formulation Examples a) A dusting agent is obtained by mixing 10 parts by weight of an active substance combination according to the invention and 90 parts by weight of talc as inert substance and comminuting the mixture in a hammer mill.

b) A wettable powder which is readily dispersible in water is obtained by mixing 25 parts by weight of active substance A+B, 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned disk-mill.

c) A dispersion concentrate which is readily dispersible in water is obtained by mixing 20 parts by weight of active substance A+B with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of active substance A+B, 75 parts by weight of cyclohexanone as the solvent and 10 parts by weight of oxethylated nonylphenol as the emulsifier.

e) Water-dispersible granules are obtained by mixing 75 parts by weight of active substances A+B, 10 parts by weight of calcium ligninsulfonate, 5 parts by weight of sodium lauryl sulfate, 3 parts by weight of polyvinyl alcohol and 7 parts by weight of kaolin, grinding the mixture in a pinned disc mill, and granulating the powder in a fluidized bed by spraying on water as the granulation liquid.

f) Water-dispersible granules are also obtained by homogenizing and precomminuting 25 parts by weight of active substance A+B, 5 parts by weight of sodium2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water on a colloid mill, subsequently grinding the mixture on a bead mill, and atomizing and drying the resulting suspension in a spray tower by means of a single-substance nozzle.

B. Biological examples

A range of economically important weeds and grass weeds were grown under natural field conditions. After they had reached certain development stages (expressed by the number of unfolded leaves or by the plant height), the herbicide mixtures were applied by means of specific plot sprayers. As rule, 300–400 liters of water were used per hectare, and the slurry was applied at a pressure of 2.5 bar.

Over a period of 3–8 weeks after the application, the herbicidal activity of the treated part-plots were assessed by comparing them with untreated control plots by visual scoring. This included assessment of the damage and the development of all aerial parts of the plants.

In the combinations, a distinction was made between the calculated and the found degree of effectiveness. The calculated degree of effectiveness, which is to be expected theoretically, of a combination is determined by S. R. Colby's formula: Calculation of synergistic and antagonistic responses of herbicide combinations, Weeds 15 (1967) 20–22.

This formula reads:

$$E = X + Y - \frac{X \cdot Y}{100}$$

where

X=% damage by herbicide A at a dosage rate of x kg/ha;

Y=% damage by herbicide B at a dosage rate of y kg/ha;

E=damage to be expected by herbicides A+B at dosage rates of x+y kg/ha.

If the actual damage is greater than the damage to be expected from the calculations, then the action of the combination is superadditive, i.e. a synergistic effect of action is present.

In most cases, however, the synergistic total increase in action is so high that Colby's criterion can be dispensed with; in this case, the reaction of the combination noticeably exceeds the formal total (total in figures) of the actions of the individual substances.

It must be expressly stated that an assessment of the synergism in the active substances used here must take into account the dosage rates of the individual active substances, which vary greatly. It would therefore not make sense to compare the action of the active substance combinations and the individual active substances at in each case identical application rates. The quantities of active substance which can be saved according to the invention are only noticeable in the case of superadditive increased action when the combined dosage rates are applied, or when the application rates of both individual active substances in the combination are reduced compared with the individual active substances, while having the same effect in each case.

Example 1

TABLE 1

| Combination (A1-1) + (B1) on *Cyperus rotundus* | | |
|---|---|---|
| Herbical active substance | Dosage rate in g ai/ha | Action in % |
| (A1-1) | 400 | 0 |
| | 800 | 30 |
| | 1200 | 53 |
| | 1500 | 55 |

TABLE 1-continued

| Combination (A1-1) + (B1) on *Cyperus rotundus* | | |
|---|---|---|
| Herbical active substance | Dosage rate in g ai/ha | Action in % |
| (B1) | 30 | 5 |
| | 60 | 5 |
| | 120 | 25 |
| (A1-1) + (B1) | 400 + 30 | 35 |
| | 400 + 60 | 55 |
| | 400 + 120 | 68 |
| | 800 + 30 | 90 |
| | 800 + 60 | 90 |
| | 800 + 120 | 96 |
| | 1200 + 30 | 92 |
| | 1200 + 60 | 96 |
| | 1200 + 120 | 97 |

Table 1 abbreviations
ai = active ingredient (= based on pure active substance)
(A1-1) = monoammonium salt of glufosinate, added to the tankmix in the form of a 20% aqueous formulation (SL 20).
B1 = 1-[(2-ethoxyphenoxy)sulfonyl]-3-(4,6-dimethoxypyrimid-2-yl)urea, added to the tankmix in the form of a 20% water-dispersible powder.

Example 2:

Cyperus rotundus was treated shortly before anthesis (stage 51) and the damage after application was assessed (see Table 2).

TABLE 2

| Combination (A2-1) + (B1) on *Cyperus rotundus* | | |
|---|---|---|
| Herbical active substance | Dosage rate in g ai/ha | Action in % |
| (A2) | 1080 | 80 |
| | 2160 | 93 |
| (B1) | 60 | 5 |
| (A2-1) + (B1) | 1080 + 60 | 95 |

Table 2 abbreviations:
(A2-1) = monoisopropylammonium salt of glyphosate in the form of an aqueous formulation, added to the tankmix at a dosage rate of 480 g/l
(B1) = see Table 1

Example 3

The results shown in Table 3 were obtained analogously to Examples 1 and 2.

TABLE 3

| Combination (A1-1) + (B5) against perennial and annual species | | | | | |
|---|---|---|---|---|---|
| Herbicides | Dosage rate in g ai/ha | CYPRO | AMASP | TAGMI | COMBE |
| (A1) | 1000 | 85 | 100 | 100 | 97 |
| | 400 | 35 | 40 | 55 | 42 |
| (B5) | 30 | 0 | 0 | 0 | 2 |
| | 20 | 0 | 0 | 0 | 0 |
| | 10 | 0 | 0 | 0 | 7 |
| (A1-1) + | 400 + 10 | 50 | 100 | 100 | 75 |
| (B5) | 400 + 20 | 60 | 100 | 100 | 85 |
| | 400 + 30 | 80 | 100 | 100 | 87 |

Notes to Table 3:
Treatment: Post-emergence, 4–6-leaf stage to anthesis/25–50 cm height
Evaluation: 28–57 days after application TABLE 3-continued

| | Combination (A1-1) + (B5) against perennial and annual species | | | | |
|---|---|---|---|---|---|
| Herbicides | Dosage rate in g ai/ha | CYPRO | AMASP | TAGMI | COMBE |

The following were tested under natural conditions:
CYPRO = *Cyperus rotundus*
AMASP = *Amaranthus spinosus*
TAGMI = *Tagmites minor*
COMBE = *Commelina benghalensis*
(A1-1) = see Table 1
(B5) = nicosulfuron added to the tankmix in the form of a 20% water dispersible powder.

Example 4

The results shown in Table 4 were obtained analogously to Examples 1 to 3.

TABLE 4

| | Combination (A1-1) + (B5) against annual species. | | | | | | |
|---|---|---|---|---|---|---|---|
| Herbicides | Dosage rate in g ai/ha | BRSNN | MEUIN | VICVI | GALAP | POLCU | URTDI |
| (A1-1) | 600 | 72 | 98 | 92 | 0 | 92 | 50 |
|  | 300 | 20 | 25 | 42 | 0 | 57 | 10 |
| (B5) | 40 | 87 | 0 | 0 | 25 | 52 | 85 |
| (A1-1) + (B5) | 300 + 40 | 95 (E = 79) | 85 | 62 | 75 | 100 (E = 80) | 96 (E = 86) |

Notes to Table 4:
Treatment: In the 3–8-leaf stage
Evaluation: 30 days after assessment
Abbreviations:
BRSNN = *Brassica napus napus*
MEUIN = *Melilotus indicus*
VICVI = *Vicia villosa*
GALAP = *Galium aparine*
POLCU = *Polygonum cuspidatum*
URTDI = *Urtica dioica*
E = expected value using COLBY formula
(A1-1) = see Table 1
(B5) = see Table 3
ai = see Table 1

Example 5

The results in Table 5 were obtained analogously to Examples 1 to 4.

TABLE 5

| | Combination (A1-1) + (B7) | | | | |
|---|---|---|---|---|---|
| Herbicides | Dosage rate in g ai/ha | GALAP | VERPE | VIOAR | ECHCG |
| (A1-1) | 1000 | 80 | 90 | 85 | 95 |
|  | 600 | 70 | 80 | 35 | 92 |
|  | 400 | 25 | 50 | 0 | 50 |
|  | 200 | 0 | 0 | 0 | 0 |
|  | 100 | 0 | 0 | 0 | 0 |
| (B7) | 25 | 50 | 0 | 65 | 85 |
|  | 12.5 | 0 | 0 | 40 | 75 |
| (A1-1) + (B7) | 200 + 12.5 | 95 | 50 | 65 | 98 |
|  | 200 + 25 | 90 | 70 | 80 | 95 |

TABLE 5-continued

| | Combination (A1-1) + (B7) | | | | |
|---|---|---|---|---|---|
| Herbicides | Dosage rate in g ai/ha | GALAP | VERPE | VIOAR | ECHCG |
| | 400 + 12.5 | 98 | 90 | 89 | 90 (E = 88) |
| | 400 + 25 | 80 | 93 | 97 | 98 (E = 92) |

Abbreviations:
GALAP = *Galium aparine*
VERPE = *Veronica persicaria*
VIOAR = *Viola arvense*
ECHCG = *Echinochloa crus galli*
(A1-1) = see Table 1
(B7) = 1-[3-(N-methyl-N-methylsulfonylamino)-pyrid-2-yl-sulfonyl]-3-(4,6-dimethoxy pyrimid-2-yl)urea
Application: In the 1–8-leaf stage;
Evaluation: 6 weeks after application

We claim:

1. A herbicidal composition with herbicidally effective content of a combination of A) a compound of the formula (A1)

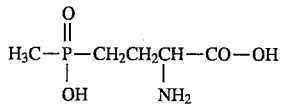

or salts thereof and

B) one or more compounds of the formula (B)

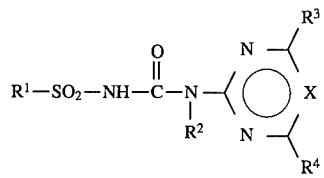

where

R$^1$ is a radical selected from the group consisting of 3-(dimethylaminocarbonyl)pyrid-2-yl, 3-ethylsulfonylpyrid-2-yl and 3-[N-($C_1$–$C_4$-alkyl)-N-($C_1$–$C_4$-alkylsulfonyl)amino]pyrid-2-yl, R$^2$ is H or methyl, R$^3$ and R$^4$ independently of one another are $C_1$–$C_2$-alkyl, $C_1$–$C_2$-alkoxy or $C_1$–$C_2$-haloalkoxy and X is CH or N, or salts thereof.

2. A composition as claimed in claim 1, which contains, besides customary formulation auxiliaries, 0.1 to 99% by weight of the active substances A1 and B.

3. A composition as claimed in claim 1, which contains the active substances A1 and B in a ratio by weight of 1500:1 to 1:10.

4. A composition as claimed in claim 3, in which the ratio by weight is 200:1 to 1:2.

5. A composition as claimed in claim 1, prepared by formulating a compound A1 with one or more compounds B in a customary crop protection agent formulation from the group consisting of wettable powders, emulsifiable concentrates, aqueous solutions, emulsions, sprayable solutions (tank mix), dispersions on an oil or water base, suspoemulsions, dusting agents, seed-dressing agents, soil granules or granules for broadcasting, water-dispersible granules, ULV formulations, microcapsules and waxes.

6. Method of controlling undesired plants, which comprises applying a herbicidally effective amount of one of the combinations of active substances A1+B, as defined in claim 1, to these plants.

7. The method as claimed in claim 6 in which the dosage rates for the compound A1 are from 10 to 2500 g/ha and the dosage rates for the compounds B are from 2 to 200 g/ha.

8. A herbicidal composition with herbicidally effective content of a combination of A) a compound of the formula (A2)

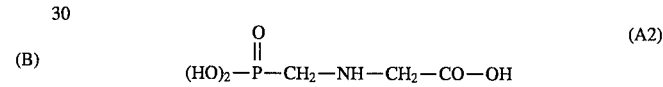

or salts thereof and

B) one or more compounds of the formula (B)

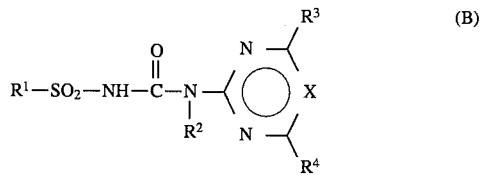

where

R$^1$ is a radical selected from the group consisting of 2-ethoxyphenoxy, 2-propoxyphenoxy, 2-isopropoxyphenoxy, 3-(dimethylaminocarbonyl) pyrid-2-yl, 3-[N-($C_1$–$C_4$-alkyl)-N-($C_1$–$C_4$-alkylsulfonyl)amino]-pyrid-2-yl and (N-methyl-N-methylsulfonyl)aminosulfonyl, R$^2$ is H or methyl, R$^3$ and R$^4$ independently of one another are $C_1$–$C_2$-alkyl, $C_1$–$C_2$-alkoxy or $C_1$–$C_2$-haloalkoxy and X is CH or N, or salts thereof.

9. A composition as claimed in claim 8, which contains, besides customary formulation auxiliaries, 0.1 to 99% by weight of the active substances A2 and B.

10. A composition as claimed in claim 8, which contains the active substances A2 and B in a ratio by weight of 1500:1 to 1:10.

11. A composition as claimed in claim 10, in which the ratio by weight is 200:1 to 1:2.

12. A composition as claimed in claim 8, prepared by formulating a compound A2 with one or more compounds B in a customary crop protection agent formulation from the group consisting of wettable powders, emulsifiable concentrates, aqueous solutions, emulsions, sprayable solutions (tank mix), dispersions on an oil or water base, suspoemulsions, dusting agents, seed-dressing agents, soil granules or granules for broadcasting, water-dispersible granules, ULV formulations, microcapsules and waxes.

13. Method of controlling undesired plants, which comprises applying a herbicidally effective amount of one of the combinations of active substances A2+B, as defined in claim 8, to these plants.

14. The method as claimed in claim 13 in which the dosage rates for the compound A2 are from 10 to 2500 g/ha and the dosage rates for the compounds B are from 2 to 200 g/ha.

* * * * *